(12) United States Patent
Braterman et al.

(10) Patent No.: US 7,550,099 B2
(45) Date of Patent: Jun. 23, 2009

(54) METAL HYDROXIDE DERIVATIVES CONTAINING CHEMICALLY BOUND ORGANOPHOSPHORUS OR POLYPHOSPHATE SPECIES AS FLAME RETARDANTS

(75) Inventors: Paul S. Braterman, Denton, TX (US);
Nandika D'Souza, Denton, TX (US);
Amit Dharia, Irving, TX (US)

(73) Assignee: University of North Texas, Denton, TX (US)

( * ) Notice: Subject to any disclaimer, the term of this patent is extended or adjusted under 35 U.S.C. 154(b) by 520 days.

(21) Appl. No.: 11/392,361

(22) Filed: Mar. 29, 2006

(65) Prior Publication Data
US 2006/0219991 A1    Oct. 5, 2006

Related U.S. Application Data

(60) Provisional application No. 60/666,343, filed on Mar. 29, 2005.

(51) Int. Cl.
*C09K 21/00* (2006.01)
(52) U.S. Cl. .................. 252/609; 252/601; 252/610; 423/299; 423/306; 523/205
(58) Field of Classification Search ............ 252/601, 252/609, 610; 523/205; 423/299, 306
See application file for complete search history.

(56) References Cited

U.S. PATENT DOCUMENTS

| 4,729,854 A | * | 3/1988 | Miyata et al. ............... 252/609 |
| 5,730,951 A | * | 3/1998 | Martin et al. ............ 252/518.1 |
| 6,291,570 B1 | * | 9/2001 | Katsuki et al. ............. 524/434 |
| 2003/0158319 A1 | | 8/2003 | Stelandre et al. |

FOREIGN PATENT DOCUMENTS

EP    0 656 634 A2    6/1995

OTHER PUBLICATIONS

PCT Notification of Transmittal of the International Search Report and the Written Opinion of the International Searching Authority, or the Declaration dated Oct. 5, 2006.

* cited by examiner

*Primary Examiner*—Mark Kopec
*Assistant Examiner*—Haidung D Nguyen
(74) *Attorney, Agent, or Firm*—Jackson Walker L.L.P.

(57) ABSTRACT

Novel metal hydroxide derivatives which chemically combine positively charged metal hydroxide layers with negatively charged phosphorus-containing species, which can be either anionic organophosphorus materials or phosphorus-containing polymeric anions, are described. The metal hydroxide derivatives are useful flame retardants through their ability to be completely dispersed and their formation of a crust or char to prevent flame propagation.

9 Claims, 6 Drawing Sheets

METAL HYDROXIDE DERIVATIVES CONTAINING CHEMICALLY BOUND ORGANOPHOSPHORUS OR POLYPHOSPHATE SPECIES AS FLAME RETARDANTS

This application claims priority to U.S. Provisional Patent Application Ser. No. 60/666,343, entitled "Novel Metal Hydroxide Derivatives Containing Chemically Bound Organophosphorus or Polyphosphate Species as Flame Retardants," filed on Mar. 29, 2005, the entire content of which is hereby incorporated by reference.

STATEMENT OF RIGHTS TO INVENTIONS MADE UNDER FEDERALLY SPONSORED RESEARCH

Not applicable.

BACKGROUND

This invention relates to flame retardant materials, and in particular to a flame retardant material comprising metal hydroxide derivatives with chemically incorporated phosphorus-containing species.

Solid materials do not burn directly. They must first be decomposed by heat (pyrolysis) to release flammable gases. Visible flames appear when these flammable gases burn with the oxygen ($O_2$) in the air. If solid materials do not break down into gases, then they will only smolder slowly and often self extinguish, particularly if they "char" and form a stable carbonaceous barrier which prevents access of the flame to the underlying material. However, materials such as wood do in fact burn vigorously, because once ignited the heat generated breaks down long-chain solid molecules into smaller molecules which transpire as gases. The gas flame itself is maintained by the action of high energy "radicals" (for example, H and OH in the gas phase) which act as intermediates in reaction sequences whose overall effect is reaction of the burning material with oxygen in the air to produce $CO_2$ and water, thus generating heat energy. Thus, effective flame retardant materials often act to promote "charring" and/or to eliminate high energy radicals.

Metal hydroxides are among the most used flame retardants. This is due to a low cost compared to antimony-halogen systems and phosphorus-based flame retardants. Inorganic hydroxides are easily handled and relatively non-toxic. These classes of materials provide flame-retardant formulation that meet appropriate standards for many applications. Such formulations have low opacity, low toxicity, and minimal corrosivity.

Properly compounded, inorganic hydroxides offer a cost-effective way to achieve low-smoke flame-retardant formulations with low tendency for non-thermal damage. Aluminium trihydroxide (ATH) is the most commonly inorganic hydroxide used as flame retardant. It is suitable for elastomers and thermosetting resins, and thermoplastics processed below 200° C. Magnesium hydroxide (MH) is a more thermally stable inorganic flame retardant. It is stable above 300° C. and can be used in many elastomers and resins, including engineering plastics and other resins processed at higher temperatures.

Metal hydroxides contribute to several flame retardant actions. They first decompose endothermally and release water. The endothermic decomposition acts as a "heat sink" that cools the substrate and decreases the pyrolysis of the polymer (physical action in the condensed phase). The release of water dilutes the amount of fuel and avoids the critical fuel/oxygen-ratio (physical action in the gas phase). Both essentially fight against ignition. In some fire tests, the ignition has to be strongly delayed. Thus, metal hydroxides are suitable for these applications. Moreover, after the degradation, a ceramic-based-protective layer is created. This ceramic-based layer improves the insulating property (physical action in the condensed phase) and reveals a smoke suppressant effect (chemical action in the condensed phase). The ceramic-based protective layer ensures an efficient protection of the polymer during the combustion leading to a severe decrease of the heat release.

Layered double hydroxides ("LDH"), which may be referred to as hydrotalcite ("HT") compounds, are used extensively as flame retardants. In particular, LDH as magnesium aluminum carbonate is used extensively as an additive to PVC. LDH works as a filler, undergoes endothermic decomposition in several steps, releases steam and carbon dioxide, and soaks up HCl from the decomposing polymer. The LDH material must also be treated to improve crystallinity and aid deaggregation and dispersion. LDH is capable of incorporating borate, trimetaphosphate, and anions containing phenyl and benzyl groups. These may act as potential char promoters and free radical terminators.

Phosphorus containing flame retardants usually act in the solid phase of burning materials. When heated, the phosphorus reacts to give a polymeric form of phosphoric acid (nominally $HPO_3$). This acid causes the material to char, inhibiting the "pyrolysis" process (break down and release of flammable gases) which is necessary to feed flames.

Different phosphorus containing flame retardants can be either simply mixed into plastics (and then held in the material when the plastic sets) or be reactive, and chemically bind into the plastic molecules at polymerization. This will depend on the properties required of the plastic in terms of finished product performance, facility of processing (melting, extrusion, moulding) and flame retardancy (temperature of onset of the charring process). Phosphorus based flame retardants vary from elemental red phosphorus (P), which is oxidized to phosphoric acid with heat, to complex P-containing organic molecules offering specific performance properties. Certain products contain both phosphorus, halogen, and/or nitrogen, thus combining the different flame retarding mechanisms of these elements.

Phosphorus-containing additives refer to a wide range of compounds. These include halogenated phosphorus and non-halogenated phosphorus compounds. Non-halogenated phosphorus compounds include red phosphorus, water-soluble inorganic phosphates, ammonium phosphate and polyphosphate, organophosphates and phosphonates and phosphine oxide. Monoammonium phosphate and diammonium phosphate achieve good FR properties in a wide range of cellulosic-based materials such as textiles, woven or non-woven, paper and wood. Ammonium and melamine phosphates and polyphosphates, often mixed with pentaerythritol, behave similarly. The mechanism is a chemical one in condensed phase. The char formation results from esterification of hydroxyl groups with the phosphoric acid. However, the solubility of such additives leads to aging problems. Red phosphorus is a very efficient flame retardant for oxygenated polymers. Coated red phosphorus is commercially used as a flame retardant for nylon electrical parts. To inhibit its ignition in the air, red phosphorus is encapsulated in a high concentration of polymer. Therefore, commercial additives never contain more than 50 wt. %. Moreover, its toxicity and red color are the reasons why its use is not extensive.

Trialkyl phosphates and dialkyl phosphonates can also be used as flame retardants. Triethyl phosphate acts as a synergistic agent in halogenated polyesters but not as efficiently as antimony oxides. Dimethyl phosphonate is a very effective flame retardant due to its high phosphorus content. However, its high volatility limits its use in rigid PU and highly filled polyester. Aryl phosphates can be used as non-flammable plasticizers for PVC and cellulose acetate and as non-halogen flame retardants for modified PPO or PC/ABS blends. Triaryl phosphates are volatile during processing which leads to stress cracking. Use of less volatile diphosphates reduces processing problems.

What is needed, therefore, is a flame retardant material comprising the functionalities of both LDH and phosphorus-containing compounds, which is evenly dispersed in small particles into polymer materials and generates a crust at flame temperature.

Phenyl phosphonate has been incorporated into LDH, as has inorganic phosphate. The resulting materials have not been investigated for their flame retardant properties. Phosphorus-containing flame retardants have been mechanically mixed into polymers alongside LDH carbonate. This is not the optimum way of combining their properties, since it is necessary to achieve dispersal of two different materials of very different wetting and contact properties, and problems arising from the volatility or solubility of the phosphorus-containing component are not resolved.

SUMMARY

The present invention relates to flame retardant materials comprising metal hydroxide derivatives with chemically bound organophosphorus or polyphosphate species. Positively charged metal hydroxide layers are chemically combined with negatively charged phosphorus-containing species, which can be either anionic organophosphorus materials or phosphorus-containing polymeric anions. In addition to the separate flame retardant properties of the metal hydroxide and the organophosphorus materials, there is a synergistic effect related to the formation of a viscous material which can act as a physical barrier between the flame region and the underlying material. In addition, the incorporation into the hybrid material greatly reduces the effective solubility and volatility of the phosphorus-containing component. Moreover, in the case that the phosphorus-containing component is an organophosphorus anion, its adhesion to the LDH will promote dispersion of the LDH into organic-based polymers.

A layered double hydroxide ("LDH") has a structure with two closely-packed metal hydroxide layers containing di- and tervalent metals. These layers are separated by an interlayer containing anion Y and loosely held water molecules. The ratio of the M(II) divalent and M(III) tervalent metals determines the charge density, which is compensated by the anionic charge of the interlayer. There is a strict relationship between the charge density M(II)/M(III), the charge of the anions, and the density with which anions are incorporated in the interlayer. Under certain circumstances, neutral molecules other than water may be incorporated into the interlayer. The thickness of the interlayer is controlled by the size, abundance, and in some cases the shape and orientation of the anions and any other incorporated material. The dispersability of the LDH particles strongly depends on particle size, shape, clustering, and the hydrophilic/hydrophobic nature. All of these factors are controllable by the preparation conditions and post-preparation treatment. The particle surface is normally hydrophilic, but may be rendered hydrophobic by surfactant treatment, including treatment with phosphorus containing surfactants.

A common chemical formula for the LDH derivatives of the current invention is:

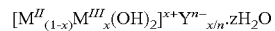

wherein $M^{II}$ and $M^{III}$ are divalent and trivalent metal cations, respectively, and $Y^{n-}$ is an anionic phosphorus-containing species. $M^{II}$ and $M^{III}$ may be a wide variety of divalent and tervalent metal cations, but a preferred $M^{II}$ is Mg and a preferred $M^{III}$ is Al. The anionic phosphorus-containing species $Y^{n-}$ can be almost anything. If the anion is a weak acid, the free acid can often be included through hydrogen bonding. In the formula, x can range from 0.2 to 0.5, and preferably ranges from 0.25 to 0.34; n can be any positive whole number, preferably ranges from 1 to 4, and more preferably ranges from 1 to 2; z can be 0 or any positive number, and preferably rages from 0 to 4.

DETAILED DESCRIPTION OF PREFERRED EMBODIMENTS

One embodiment of the current invention relates to a novel metal hydroxide derivative having the following general formula:

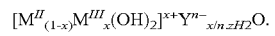

In this formula, $M^{II}$ can be any divalent metal cation, and in particular, Mg, Ni, Zn, Ca, Cu, Co, Fe, or Mn. Preferably, $M^{II}$ is Mg. The cation $M^{III}$ can be any tervalent metal cation, and in particular, Al, Fe, Cr, Mn, Co, or V. Preferably, $M^{III}$ is Al. The anion $Y^{n-}$ is an anionic phosphorus-containing species, which can be either an anionic organophosphorus material, such as an anion derived from monophenyl phosphate, or a phosphorus-containing polymeric anion. Preferably, $Y^{n-}$ is a mono- or dialkyl phosphate, a mono- or diphenyl phosphate, or polyphosphate. Organophosphonate can be used in place of organophosphate, mono-organic phosphate may be incorporated as a dianion or as a hydrogen-containing monoanion, and these materials may be incorporated singly or together. Neutral flame retardant species may also be incorporated by hydrogen bonding. Examples include mono- and dicetyl phosphate (singly or together), phenyl phosphonate, phenyl phosphate, diphenyl phosphate, and polyphosphate derived either from inorganic sources, or as compounded with ammonium ions, melamine, and/or pentaerythritol. In the formula, x can range from 0.2 to 0.5, and preferably ranges from 0.25 to 0.34; n can be any positive whole number, preferably ranges from 1 to 4, and more preferably ranges from 1 to 2; z can be 0 or any positive number, and preferably rages from 0 to 4.

The metal hydroxide derivatives may additionally be exposed to surfactants to convert the hydrophilic surface of the particles to hydrophobic. Surfactants can also be used to modify the particle growth. The surfactants can themselves be phosphorus-containing materials and can contribute to flame retardance.

An additional embodiment of the current invention relates to a novel flame retardant material comprising the metal hydroxide derivatives described above. The metal hydroxide derivatives can be completely dispersed into a range of polymers such as polyalkene, epoxy, polyvinyl and polystyrene materials. The flame retardant material possesses a synergistic improvement as the result of crust and char formation as obstacles to flame propagation. Without wanting to be bound by theory, a viscous material, which is believed to be a metal phosphate, is formed which can act as a physical barrier between the flame region and the underlying material.

Figure 1:
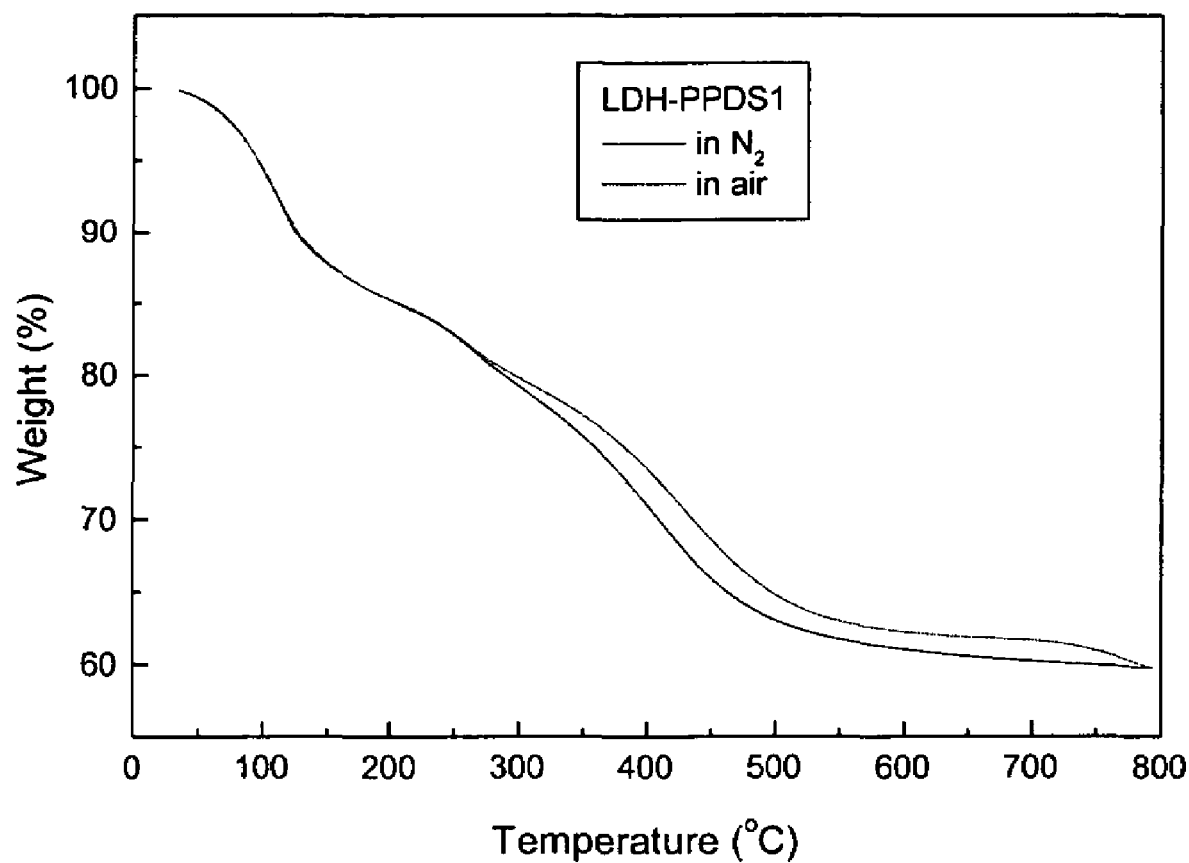
FIG. 1 shows the thermogravimetric analysis of an LDH phenyl phosphate compound.
Figure 2:
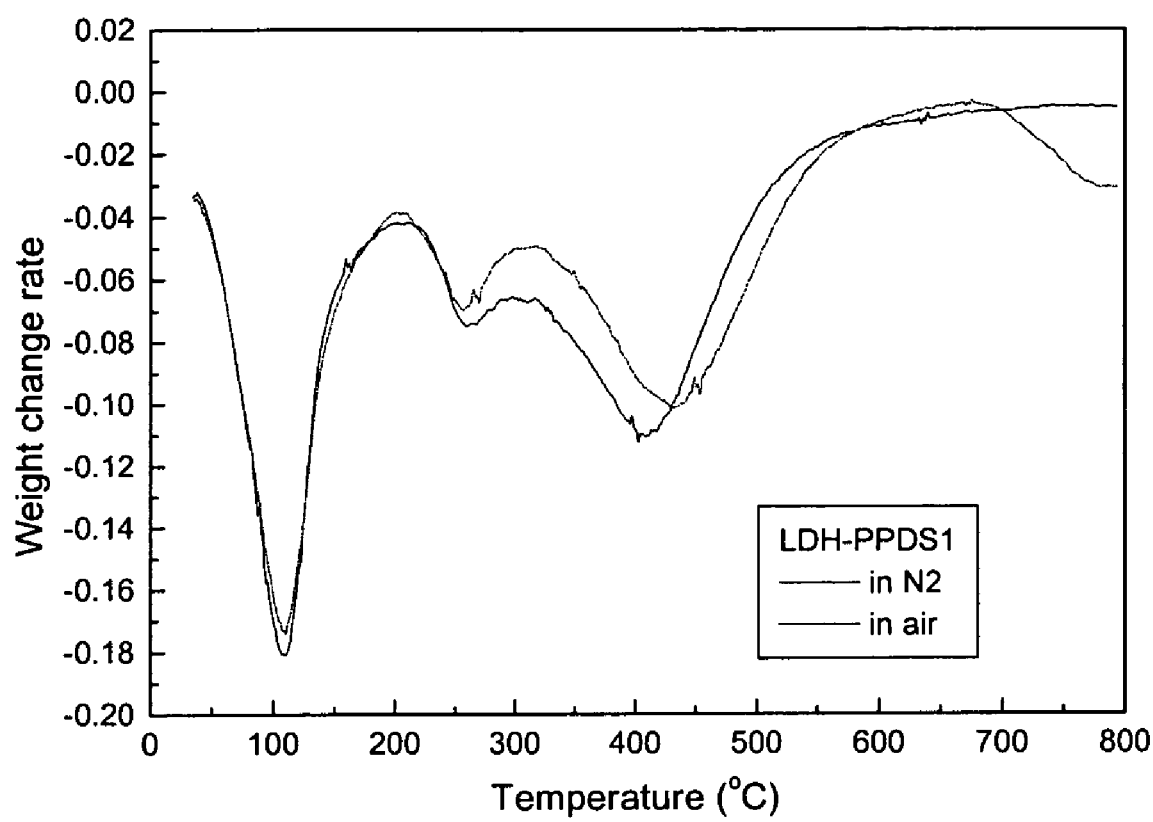
FIG. 2 shows the derivative thermogravimetric analysis of an LDH phenyl phosphate compound.

Metal hydroxide derivatives in general show weight losses due to the loss of interlayer water and of hydroxyl water in the range of about 300 to about 400° C. In addition, FIGS. 1 and 2 show, as measured by thermogravimetric analysis ("TGA") and derivative thermogravimetric analysis ("DrTGA"), that an LDH organophosphorus material (a magnesium aluminum phenyl phosphate) undergoes weight loss at a higher temperature in air than in an inert atmosphere, which indicates that a crust or char is formed to inhibit the escape of material.

A further embodiment of the current invention relates to a material having increased flame retardant properties comprising the metal hydroxide derivatives dispersed into a polyalkene, epoxy, or polystyrene material. Yet another embodiment relates to a method for increasing the flame retardant properties of a polyalkene, epoxy, or polystyrene material by dispersing the metal hydroxide derivatives into the material.

EXAMPLE 1

Synthesis of LDH-Cetyl Phosphate

LDH-Colafax 1 and LDH-Colafax 2, both of which are LDH cetyl phosphate derivatives, were synthesized using LDH-nitrate. Colafax is a commercially available anionic surfactant, containing roughly equal amounts of cetyl phosphate, $C_{16}H_{33}OP(O)(OH)_2$, and dicetyl phosphate, $(C_{16}H_{33}O)_2P(O)_2OH$.

LDH nitrate (Mg—Al—$NO_3$-LDH) was prepared according to standard procedures. 7.692 g magnesium nitrate (30 m mole, 99%, Aldrich, St. Louis, Mo.) and 3.751 g aluminum nitrate (10 m mole, 98+%, Aldrich) were dissolved in 100 ml water in a 250 ml round bottom flask and kept under nitrogen environment with continuous flowing of nitrogen. 50% w/w NaOH solution (60 m mole, Alfa Aesar, Ward Hill, Mass.) was added drop wise with continuous stirring to the metal ion solution. A white precipitate was formed and aged overnight in an oil bath at about 100° C. with continuous refluxing and stirring under nitrogen atmosphere. The precipitate was separated by centrifuging and washed several times with deionized water. It was dried in vacuum over molecular sieves at room temperature for further analysis and characterization. To create the LDH Colafax derivatives, the LDH nitrate was exposed to two different alkaline Colafax solutions. The relative amounts of mono-cetyl phosphate and dicetyl phosphate anions in the LDH-Colafax derivatives are not known.

Figure 3:
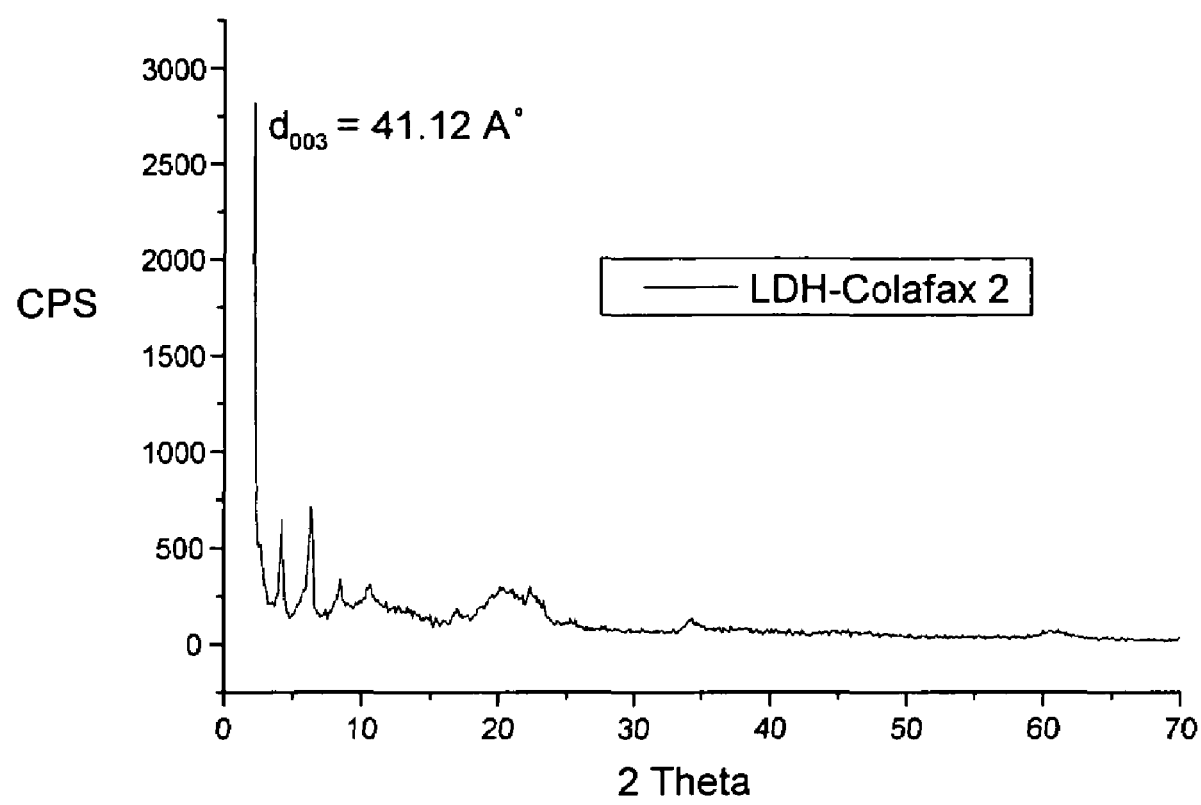
FIG. 3 shows the X-ray diffraction pattern for LDH-Colafax 2.

A first alkaline Colafax solution was used to create LDH-Colafax 2. 0.005 mole (1.61 g) Colafax CPE (Colonial Chemical, South Pittsburg, Tenn.) was dissolved in 50 ml water. It was titrated with 0.5 M NaOH solution with continuous stirring. 16 ml NaOH solution was required to reach the second end point at about pH 9.7. This solution was added to 21Mg$AlNO_3$-LDH to obtain the Colafax derivative LDH-Colafax 2. FIG. 3 shows the X-ray diffraction pattern of LDH-Colafax 2.

Figure 4:
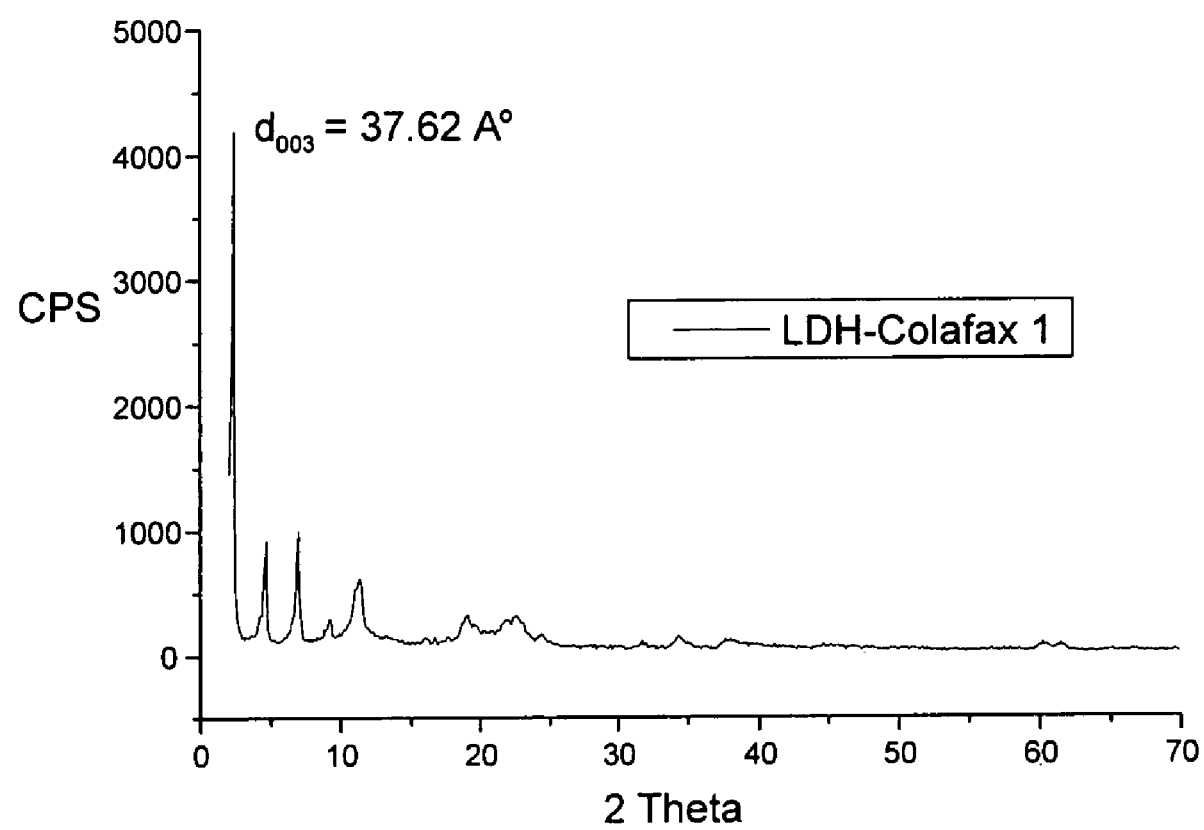
FIG. 4 shows the X-ray diffraction pattern for LDH-Colafax 1.

A second alkaline Colafax solution was used to create LDH-Colafax 1. 0.005 mole (1.61 g) Colafax CPE (Colonial Chemical) was dissolved in 50 ml water. It was titrated with 0.25 M $Na_2CO_3$ solution with continuous stirring. 26 ml $Na_2CO_3$ solution was required to reach the second end point at about pH 9.1. This solution was added to 21Mg$AlNO_3$-LDH to obtain the Colafax derivative LDH-Colafax 1. FIG. 4 shows the X-ray diffraction pattern of LDH-Colafax 1.

EXAMPLE 2

Burning Tests on Polyethylene Containing LDH-Colafax

Low-density polyethylene was mixed with the LDH Colafax derivatives described in Example 1. Samples of the mixture were then set on fire. These samples all demonstrated a char and crust that formed during burning.

EXAMPLE 3

Figure 5:
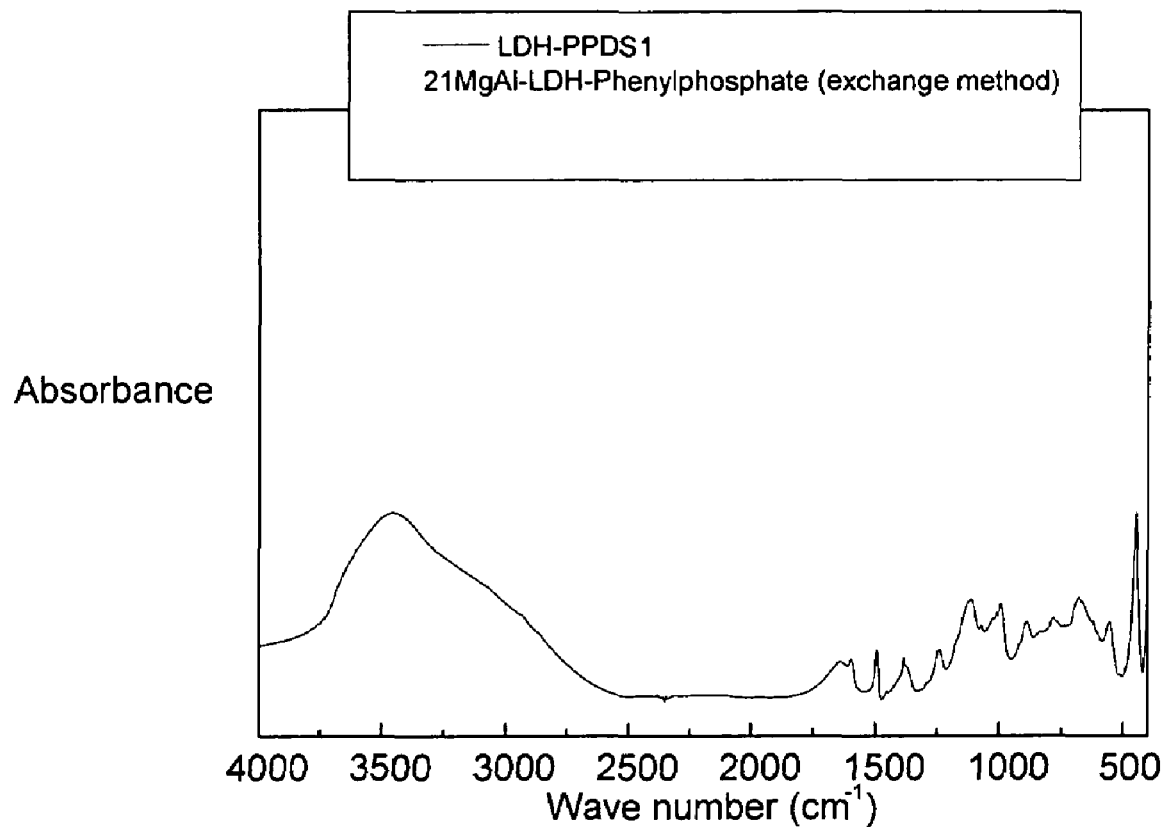
FIG. 5 shows the infrared spectrum of LDH-PPDS-1.

Preparation and Properties of LDH-Phenyl Phosphate Compounds and Exposure to Heat The LDH-phenyl phosphate compound LDH-PPDS-1 was prepared by exposing a suspension of $Mg_2Al(OH)_6NO_3$ to an aqueous solution of disodium phenyl phosphate, in a process known as the exchange method. FIG. 5 shows the infrared spectroscopy characterization of LDH-PPDS-1. Without wanting to be bound by theory, it is believed that the formula for LDH-PPDS-1 is $[Mg_2Al(OH)_6]_2O_3POC_6H_5$.

After being exposed to heat, LDH-PPDS-1 showed weight loss at a higher temperature in air than in an inert atmosphere. This indicates the formation of a crust or char that inhibits the escape of material. The results of the heat exposure of LDH-PPDS-1 are shown in FIGS. 1 and 2.

EXAMPLE 4

Preparation of LDH-Polyphosphate

Figure 6:
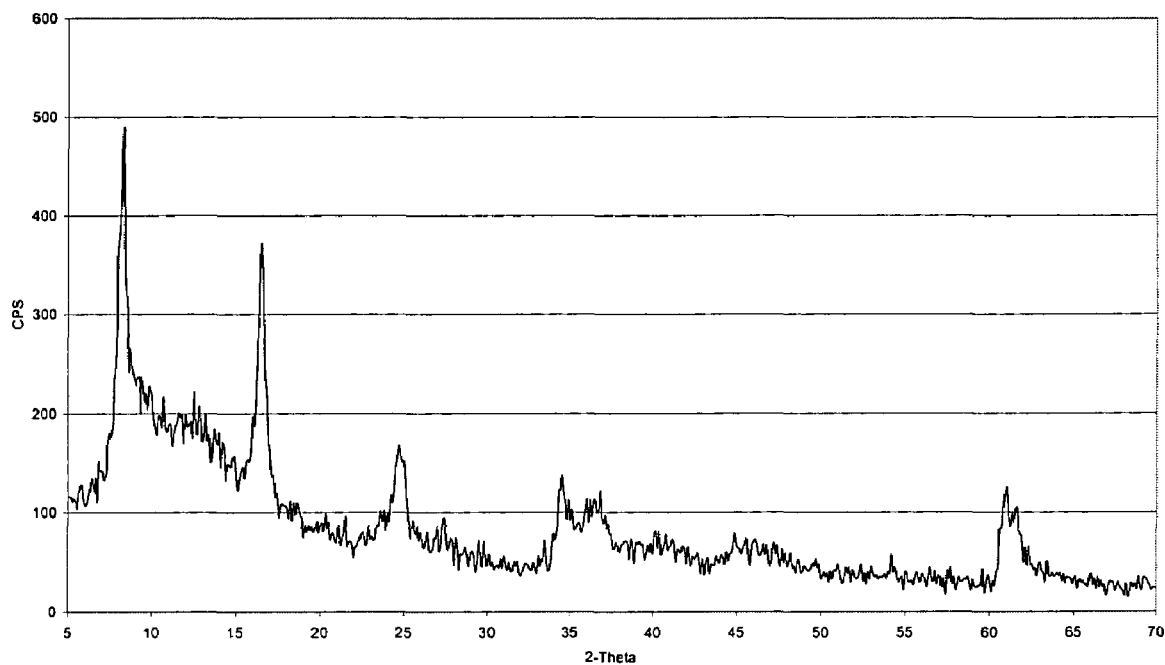
FIG. 6 shows the X-ray diffraction pattern for an LDH polyphosphate compound.

To create LDH-polyphosphate, 2 g parent 2:1 Mg—Al LDH-$NO_3$ was suspended in water. 0.4 g ammonium polyphosphate ("APP") in aqueous solution was added to the suspension. The solution was allowed to mix for 24 hours under $N_2$ at room temperature. The product was removed by filtration. X-ray diffraction, shown in FIG. 6, indicated that there was near complete exchange of nitrate by APP, with a d-spacing around 10.6 A for the d003 and 5.35 A for d006 spacings.

What is claimed is:

1. A metal hydroxide derivative comprising the general formula:

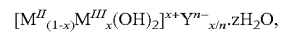

wherein, $M^{III}$ is a trivalent metal cation;

x is from 0.2 to 0.5;

n is any positive number; and z is 0 or any positive number;

$M^{II}$ is Mg, Ni, Zn, Ca, Cu, Co, Fe, or Mn;

and $Y^{n-}$ is mono-cetyl phosphate, dicetyl phosphate, or combinations thereof.

2. The metal hydroxide derivative comprising the general formula:

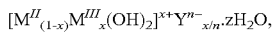

wherein,
$M^{III}$ is a trivalent metal cation;
x is from 0.2 to 0.5;
n is any positive number; and
z is 0 or any positive number;
$M^{II}$ is Mg;
and $Y^{n-}$ is mono-cetyl phosphate, dicetyl phosphate, or combinations thereof.

3. A metal hydroxide derivative comprising the general formula:

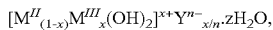

wherein,
$M^{II}$ is a divalent metal cation;
x is from 0.2 to 0.5;
n is any positive number; and
z is 0 or any positive number;
$M^{III}$ is Al, Fe, Cr, Mn, Co, or V;
and $Y^{n-}$ is mono-cetyl phosphate, dicetyl phosphate, or combinations thereof.

4. A metal hydroxide derivative comprising the general formula:

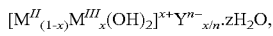

wherein,
$M^{II}$ is a divalent metal cation;
x is from 0.2 to 0.5;
n is any positive number; and
z is 0 or any positive number;
$M^{III}$ is Al, Fe, Cr, Mn, Co, or V;
wherein $M^{III}$ is Al;
and $Y^{n-}$ is mono-cetyl phosphate, dicetyl phosphate, or combinations thereof.

5. A metal hydroxide derivative comprising the general formula:

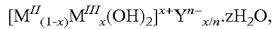

wherein,
$M^{II}$ is a divalent metal cation;
$M^{III}$ is a trivalent metal cation;
x is from 0.2 to 0.5;
n is any positive number; and
z is 0 or any positive number;
and $Y^{n-}$ is mono- or diphenyl phosphate.

6. A metal hydroxide derivative comprising the general formula:

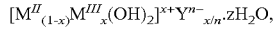

wherein,
$M^{II}$ is Mg;
$M^{III}$ is Al;
$Y^{n-}$ is mono-cetyl phosphate, dicetyl phosphate, or combinations thereof;
x is from 0.2 to 0.5;
n is any positive number; and
z is 0 or any positive number.

7. A metal hydroxide derivative comprising the general formula:

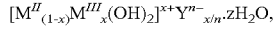

wherein,
$M^{II}$ is Mg;
$M^{III}$ is Al;
$Y^{n-}$ is mono-phenyl phosphate, diphenyl phosphate, or combinations thereof,
x is from 0.2 to 0.5;
n is any positive number; and
z is 0 or any positive number.

8. A flame retardant material comprising:
one or more polymers; and
the metal hydroxide derivative of claim 1;
wherein the metal hydroxide derivative is completely dispersed within the one or more polymers; and wherein the polymer is selected from the group consisting of polyalkene, epoxy, polyvinyl, polystyrene, and combinations thereof.

9. A method for increasing the flame retardance capabilities of a polymer material, comprising
dispersing the metal hydroxide derivative of claim 1 within the polymer material;
wherein the polymer material is selected from the group consisting of polyalkene, epoxy, polyvinyl, polystyrene, and combinations thereof.

* * * * *